(12) United States Patent
Kathariou et al.

(10) Patent No.: US 6,503,747 B2
(45) Date of Patent: *Jan. 7, 2003

(54) SEROTYPE-SPECIFIC PROBES FOR *LISTERIA MONOCYTOGENES*

(75) Inventors: Sophia Kathariou, Honolulu, HI (US); Xiang-He Lei, San Francisco, CA (US)

(73) Assignee: University of Hawaii, Honolulu, HI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/115,150

(22) Filed: Jul. 14, 1998

(65) Prior Publication Data

US 2001/0055759 A1 Dec. 27, 2001

(51) Int. Cl.[7] .......................... C07H 21/04; C12N 1/21; C12N 5/10; C12N 15/63
(52) U.S. Cl. ................. 435/252.3; 435/325; 435/320.1; 536/23.1; 536/24.32; 536/23.7
(58) Field of Search .......................... 435/252.3, 320.1, 435/325; 536/23.1, 23.7, 24.32

(56) References Cited

U.S. PATENT DOCUMENTS

| | | | |
|---|---|---|---|
| 5,089,386 A | 2/1992 | Stackebrandt et al. | 435/6 |
| 5,376,528 A | 12/1994 | King et al. | 436/6 |
| 5,389,513 A | 2/1995 | Banquero et al. | 435/6 |
| 5,491,068 A | 2/1996 | Benjamin et al. | 435/17 |
| 5,523,205 A | 6/1996 | Cossart et al. | 435/6 |
| 5,610,012 A | 3/1997 | Luchansky et al. | 435/5 |
| 5,627,030 A | 5/1997 | Pandian et al. | 435/6 |
| 5,695,946 A | 12/1997 | Benjamin et al. | 435/7.32 |
| 5,696,232 A | 12/1997 | Chakraborty et al. | 530/350 |
| 5,753,467 A | 5/1998 | Jensen et al. | 435/91.2 |

FOREIGN PATENT DOCUMENTS

| | | |
|---|---|---|
| WO | WO 96/24686 | 8/1996 |
| WO | 98/21225 | 5/1998 |

OTHER PUBLICATIONS

Morona, R. et al. J. Bacteriol. 176(3):733–747, Feb. 1994.*
Gibco/BRL Life Technologies Catalogue and Reference Guide, 1993–94, p. R100.*
Kathariou et al., "The Type Strain(s) of *Listeria monocytogenes*: a Source of Continuing Difficulties," International Journal of Systematic Bacteriology, 41(2):328–330 (1991).
Lei et al., EMBL Acc. No. AF033015, Jan. 6, 1999.
Zheng et al., "Differentiation of Epidemic–Associated Strains of *Listeria monocytogenes* by Restriction Fragment Length Polymorphism in a Gene Region Essential for Growth at Low Temperatures (4° C)", Applied and Environmental Microbiology, 61(12):4310–4314 (1995).
Lei, Xiang–He et al., "*Listeria monocytogenes* Serotype 4b–Specific PCR Detection," abstacts of the General Meeting of the American Society for Microbiology, 96(0):375 (1996).
Brosch et al., "Pulsed–Field Fingerprinting of Listeriae: Identification of Genomic Divisions for *Listeria monocytogenes* and Their Correlation with Serovar," Appl. Environ. Microbiol., 60(7):2584–2592 (Jul. 1994).
Lei et al., "DNA Fragments from Regions Involved in Surface Antigen Expression Specifically Identify *Listeria monocytogenes* Serovar 4 and a Subset Thereof: Cluster IIB (Serotypes 4b, 4d, and 4e)," Appl. Environ. Microbiol., 63(3):1077–1082 (Mar. 1997).

* cited by examiner

*Primary Examiner*—Carla J. Myers
*Assistant Examiner*—Diana Johannsen
(74) *Attorney, Agent, or Firm*—Richard F. Trecartin; Todd A. Lorenz; Dorsey & Whitney LLP

(57) ABSTRACT

Recombinant nucleic acids comprising region(s) of *Listeria monocytogenes* genome that are unique to an individual serotype and genomic cluster are provided. Also provided are oligonucleotide probes and primers derived from the recombinant nucleic acid sequences and methods for their use in the detection and identification serovar 4 and genomic cluster IIB strains.

12 Claims, 7 Drawing Sheets

FIGURE 1
A.
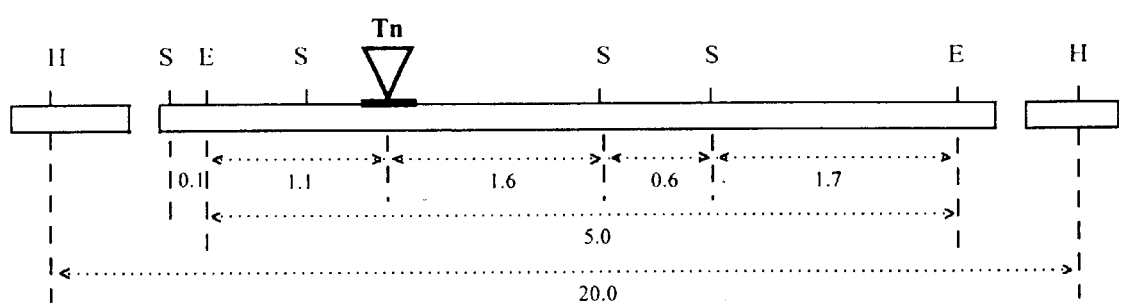
Probe 1, pXL7-1
B.
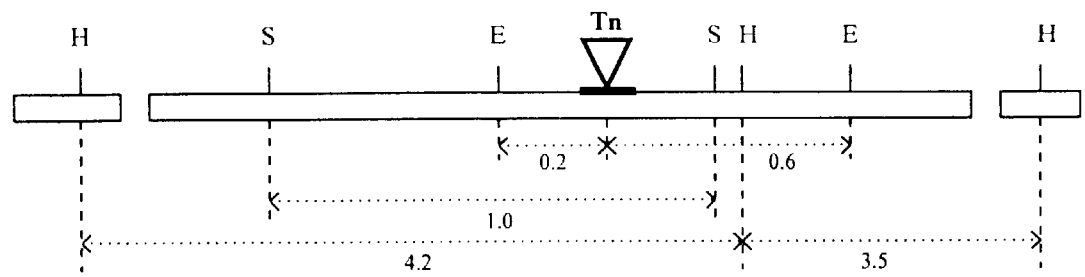
probe 2, pNP1

FIGURE 5A

```
  1 CAAAGAGTGA TTTATCTGGC AGGCAAAACG TTGTCTAACT AGTAAATTTA AAGCGAGTCC TTATCTTTTT CAAGTAAGGG
 81 CTCGCTTTAA ATTTCAATTG CGCTAGCATC TTTTTTTTGC TATATTAAAG GATAGTAACG TCTCATATAG GGAGTGGAGA
161 AAAAGAGTGT TAAATAAAAA AAGAGTTATA GTTGGGGTTT TGCTACTATT ACTAAGTTTA ATTTCTATTA GCTATTATTC
241 AGAAACCTTT AAACTAACTT TAAGCTGGTT GTTATTTGCA GTAGTTTTAA CGGTTCTTTA TTTTAGACAA GAGAAAAACT
321 TTCAATTTCA ATGGTCAACA TTGATAACCT CACTAATAAT TAGTTTATTT TGGATGGCTT CATCATTCAA TGGTGGACCA
401 TATGCGGGA ATTTTGTTTT TAATAGTAAG ATTTTAGCAG GAACTTTTCT TGTAATCACT ATCTTTGTTT TACTTTTATT
481 ACTTGAAATG CGAACGAAT ATAAAGCAAG ACCGAATCGC AAAGTAAAAT GGCCATTTTT CGCACTATTT ACGAGTATTC
561 CATTCGTGGT CTGGATGATT TCATTTCTAG CCTATTATCC AGCAAAAATG ACATTTGACT CCTATTACCA ATGGGGAATG
641 GCTCACGGTA TTCGCCAATA TAGTCAGTGG CATCCGCTTT TACACACTTT GTGGATAGAA ACAACAAGTG CGATTTACGA
721 CTCACCTTCG AGTTACATTT TTTCTCAAAT AATTGTTGTT TCATTAATCG TTGGCTTTGC TATTTATACT CTTGTAAAAA
801 TGGGCGCGCA TATTTGGATT GGTGTTTGTA TTTCAATCGG CTATGCCATT TACCCTGCAG CAATGTTTTA TTCTGCAACA
881 GCATGGAAAG ATTTTCCATT TGCAGCCTTT AATTTTAAAA TACCCGAACCT AATCCATTAA ATAGTACAAT CTAATGGAAT
961 GTGGCTGAAA AATTGGTGGC ACCTTATCGC TTTTGTTTTA GTAGCTTTTG TTTGTATAAA TTTACGAAAC AATGAATGA
1041 TGATTATCAT CGTATCGCTT CTGTGCTTGC TTATTTTCAT GAAAAACTTT CGTCTTATTA TTACCGGTAT TCTTGTTGGA
1121 ACCTTGGGAC TGAATTTTTT ATTTGGTCTG GTTATGACAA ACGGGCTTAA TGCGCAACCT AATCATTAA ACCAAGCGCT
1201 AGCAATTCCT TCCCAACAAA TTGGGGCTAC TTTTTTACAT GATGAAACT TTACTCCTGA ATTAAAAGAG TATTTCACTTT
1281 CCATATTACC TGAAGAAAAT TGGAAAAAAG ATTACAACCC TTATACTGTA GACCCAATTA AGCATGATAC CAAATACAAT
1361 TCATCCGTCA TTGAAGATGA TTTTGGACTA TACATTAAAA ATTGGTTCAA ACTCTTAACG GCTAATTTCG GTACTTATGT
1441 AGGGGCTTAT AGATACAGA TATGATGTGA TTGGCATTCG CAAATTCTTC CCAGAAGGTT TATCGGAAGA AGAGATTAAT
1521 CGAATATTCA AAATTAGGAT ATGAAGTCTA TACAAAAATG CAACTGGAAA AGATGCTGTT AGCTACAATG AGTATAAGAG
1601 AAATTAGGAT ACGGATTGAT GACTCTACTA ATCCCCTTAT TTCAATATCT AAAGCTCCAA GTCTGAAGAA AATAACAGAT AGCATTATG
1681 ACGGATTGAT GACTCTACTA ATCCCCTTAT TTCAATATCT AAAGCTCCAA GTCTGAAGAA AATAACAGAT AGCATTATG
1761 CAAAAACAAC AAATGAGTGG CAAAATTATT TATTAAAAGG AGCCATTCCA TTGTCTGAGT AATGGCACTT TCATAATAGC AATTGCTGCC
1841 GTCTGCCTCC GACTTTAGAT ATTCTTATAG TTTTATTTTC ACCCTGTAGT AATGCCACTT ATTACTATAG CAATCGCAAT
1921 GCCAGCAACA CAACTTTTAA GGAGAGAATA ATGGGAATTC ACGTGCTGTA CTCTTGCCTT GTTATAACGA
2001 ACAAAGAAAA TCAATTTTAA ATGGTAAGG TAATTGATGA TTTTAAGAAA TAAATGAGAA ATGCAGCTTA CTCTTGCCTT GTTATAACGA
2081 GGAGCTTACA ATGGTAAGG TAATTGATGA TTTTAAGAAA GAATTACCAA ATGCAGCTTA CTCTTGCCTT GTTATAACGA
2161 CTAAAGATAA ACCTTTGAA ATAGCGAAAG ATCATGGTGC TATCGTTCGA AAAGAAATGC GCCAAGGTAA AGTAATGTA
2241 GTACGTTCTA TGTTCGCGGA TATAGATGCT GATTACTATT TAATGGTCGA TGGTGACGAT ACCTATCCAG CAGAATACTG
2321 CCATGAAATA TTAGAGGTGC TTCGCAATAA GGAAGCTAAT ATGGTTATTG GTGATCGTCT GAGTAATGGT ACCTACACTG
2401 AAGAAAATAA AGAAATTT CATGACTTTG GTAACTCACT AGTACGTAAT ACAATTAATC GTATCTTCAA AAGTAATTTG
2481 AGAGATATCA TGACAGGCTA CCGTGGCTTT GATCGTTATT TGTTAAGAC TATGCCAGTT TTAAGCCCTG GTTTTGAGAT
2561 TGAAACTGAG ATGAGCATTC ACGCATTGGA AAATCGCTTT TTAGTGAAAG AAATTGAAAT TGATTACCGT GATCGTCCAG
2641 AAGTAGTGA ATCAAAACTA AACACTTTTT CTGATGGTTT CAAGTAATT ATGACGATTG TAAGATTATT TAAAATAGT
2721 CGTCCGTTTT TATTTTTCAA TTTATTAGCC TCTTTGTTTG TGCTTGTAGG AGTTCTAGTT GGTTTGCCAG TCATAATTCA
2801 GTTTCGTCAA ATTGGCTTGG TACTAAAATT TCCGAGTGCA CTGTTTTAAT CTGGTTTAAT CATAATGGGT ATGCTGTTCT
2881 TCATTTGTGT ATTAATCCTT GATACGATAG CTCATAGAAG TACTTCTTAG AACTTGTTAA ATACCGCGAA
2961 AGAAATCCAT TGAACTAAAG TTAGCCAATA AAAGAGTCGA CAGACAAAGC CAGGAAATCG ACTCTTTTAT TTATATCGGT
3041 ACTACAATTG TTCTACTGTT
```

FIGURE 5B

```
ORF-1
          10         20         30         40         50         60         70         80
          |          |          |          |          |          |          |          |
   1 MASSFNGGPY GGNFVFNSII LAGTFLVITI FVLLLLLEMR TEYKARPNRK VKWPFFALFT SIPFVVWMIS FLAYYPAKMT  80
  81 FDSYYQWGMA HGIRQYSQWH PLLHTLWIET TSAIYDSPSS YIFSQIIVVS LIVGFAIYTL VKMGAHIWIG VCISIGYAIY 160
 161 PAAMFYSATA WKDFPFAAFI LLFTVLILKI VQSNGMWLKN WWHLIAFVLV AFVCINLRNN GMMIIVSLL CLLIFMKNFR 240
 241 LIITGILVGT LGLNFLFGLV MTNGLNAQPN PLNQALAIPS QIGATFYND GNFTPELKEY FTSILPEENW KKDYNPYTVD 320
 321 PIKHDTKYNS SVIEDDFGLY IKNWFKLLTA NFGTYVGAYL DQTAVIWQFY SPENYKVFFD TSANIQDTRY DVRAFAKFFP 400
 401 EGLSEEEINK LGYEVYQNEY KNATGKDAVS YNEYKRRIDD STNPLISISK APSLKKITDS IYAKTTNEWQ NYLLKGAIPL 480
 481 VLLIIAIAAV CLQRPKKKLL IFAPVVMALI TIAIAMPATD FRYSYSFIFT VPIVFFATKL KNYKENQFZ            549
          |          |          |          |          |          |          |
          10         20         30         40         50         60         70
```

```
ORF-2
          10         20         30         40         50         60         70         80
          |          |          |          |          |          |          |          |
   1 MGILNEKVAV LLPCYNEELT IGKVIDDFKK ELPNADIYVY DNNSKDKTFE IAKDHGAIVR KEMRQGKGNV VRSMFADIDA  80
  81 DYYLMVDGDD TYPAEYCHEI LEVLRNKEAN MVIGDRLSNG TYTEENKRNF HDFGNSLVRN TINRIFKSNL RDIMTGYRGF 160
 161 DRYFVKTMPV LSPGFEIETE MSIHALENRF LVKEIEIDYR DRPEGSESKL NTFSDGFKVI MTIVRLFKNS RPFLFFNLLA 240
 241 SLFVLVGVLV GLPVIIQFAQ IGLVLKFPSA LLATGLIIMG MLFFICGLIL DTIAHRSRQS YFLELVKYRE RNPLNZ     316
          |          |          |          |          |          |          |
          10         20         30         40         50         60         70
```

SEROTYPE-SPECIFIC PROBES FOR *LISTERIA MONOCYTOGENES*

FIELD OF THE INVENTION

The present invention relates to the identification and characterization of novel DNA sequences that are specific to *Listeria monocytogenes* strains that are commonly associated with human disease and provides improved oligonucleotides and methods for their use in the detection and typing of these strains.

BACKGROUND

*Listeria monocytogenes*, a bacterium, is the causative agent of listeriosis, a serious disease of humans and animals that can be transmitted by means of contaminated food. Newborns, the elderly, and immunocompromised individuals are especially prone to infection. Listeria are commonly found in the environment and, unlike most other human pathogens, are capable of growth at refrigeration temperatures, often leading to problematic contamination of cold-stored foods. Such foods, especially dairy products, have been implicated in numerous cases of sporadic listeriosis as well as several common-source epidemics of the disease.

Even though numerous serotypes of *L. monocytogenes* have been identified with the antigenic scheme of Seeliger and Höhne (Methods Microbiol. 13:31–49 (1979)), three serotypes (1/2a, 1/2b, and 4b) account for the vast majority of clinical isolates. Furthermore, strains of serotype 4b have been implicated in a large fraction (ca. 40%) of sporadic listeriosis cases and virtually all common-source outbreaks reported in Europe and North America during the past 20 years (Schuchat et al. 1991. Clin. Microbiol. Rev. 4:169–183). Pulsed-field fingerprinting of chromosomal DNA has revealed that serotypes 4b, 4d, and 4e strains constitute one genomic subdivision (cluster IIB) (Brosh et al. 1994. Appl. Environ. Microbiol. 60:2584–2592). From the perspective of human disease, serotype 4b strains are the major component of this genomic cluster because serotype 4d and 4e strains are isolated only rarely from foods and virtually never from patients (Farber et al., 1991. Microbiol. Rev. 55:476–511).

Serologic methods currently employed to type strains of *Listeria monocytogenes* requires culturing and isolating the bacteria and highly specific antisera. These techniques are performed effectively only in a small number of reference laboratories (Seeliger and Hohne. 1979. Methods Microbiol. 13:31–49). Monoclonal antibodies have been described that are specific for individual serotypes; however, because monoclonal antibodies are highly specific, subtle variations in epitope structure can render them non-reactive. Existing hybridization and PCR-based methodologies employing oligonucleotides have been described to identify *Listeria monocytogenes* but these methods can not be used to identify individual strains and serotypes most commonly associated with human disease because the nucleic acids targeted by the oligonucleotides are shared across serotypes. As described above, pulse-field fingerprinting has been used to identify *L. monocytogenes* genomic divisions, which have been correlated with individual serovars and subgroups but this technique is not amenable to routine analysis because it requires expensive equipment to run the assay and analyze the data, and is labor intensive. It would, therefore, be useful to identify and characterize genetic and molecular features unique to *L. monocytogenes* serotypes to facilitate the development of methods and reagents for molecular subtyping and detection of strains most commonly associated with human disease.

SUMMARY OF THE INVENTION

The present invention provides compositions and methods for detecting and identifying *Listeria monocytogenes* genomic cluster IIB strains which are commonly associated with human disease.

In one embodiment the invention provides an isolated nucleic acid of *L. monocytogenes* genomic DNA that is unique to genomic cluster IIB strains.

In one aspect, the isolated nucleic acid comprises DNA having preferably at least about 80% sequence identity, and most preferably at least about 90% sequence identity to genomic cluster IIB DNA or its complement. In another aspect, the invention provides recombinant nucleic acids that hybridize to genomic cluster IIB-DNA. Preferably, hybridization occurs under stringent hybridization and wash conditions.

In another aspect the invention provides an isolated nucleic acid molecule comprising a DNA encoding one or more polypeptide(s) involved in the expression of cluster IIB polypeptides or its complement. The invention further provides antibody which specifically binds to a genomic cluster IIB polypeptide.

In a still further aspect the invention provides a vector comprising an isolated nucleic acid comprising genomic cluster IIB-DNA or its variants.

In yet another aspect the invention provides methods for detecting *L. monocytogenes* genomic cluster IIB in a composition of matter comprising cluster IIB specific nucleotide sequences. In a further aspect of the invention, oligonucleotide probes derived from the aforemention sequences and methods for their synthesis, labeling and use in the detection and identification of *L. monocytogenes* cluster IIB strains are provided. In a broad embodiment, the methods comprise contacting the nucleic acids of *L. monocytogenes* with one or more oligonucleotides under conditions permitting hybridization and detecting the hybridized oligonucleotide.

BRIEF DESCRIPTION OF THE DRAWINGS

FIG. 1. Restriction map of the DNA regions surrounding the transposon insertions in mutants XL7 (Panel A) and M44 (Panel B). E, EcoRI; H, HindIII, S, Sau3AI; Tn, transposon Tn916ΔE. Cloned DNA fragments used to construct the probes are indicated. The region which harbors transposon insertions in other mutants of the same phenotype is indicated by boldface type. The relative orientation of the last two Sau3AI fragments in Panel A has not yet been confirmed. The numbers indicate size of fragments in kilobases.

FIG. 5 Panel A: 3060 base pair unique nucleotide sequence of *L. monocytogenes* genomic cluster IIB (SEQ ID NO:1). Panel B: The deduced amino acid sequence of two open reading frames, ORF-1 (SEQ ID NO:4) and ORF-2 (SEQ ID NO:5), found within SEQ ID NO:1 that are involved in the expression of epitopes recognized by MAbs c74.22 and c74.33, respectively.

Figure 2:
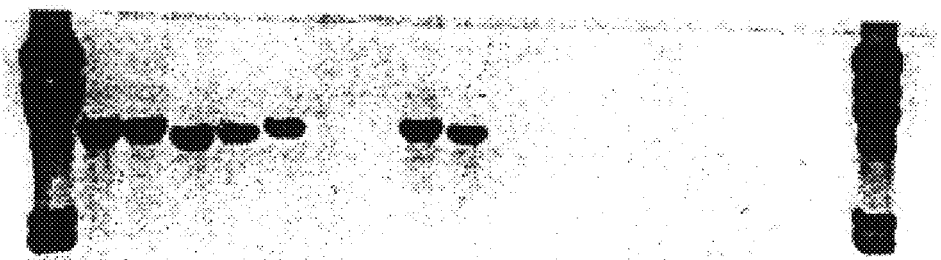
FIG. 2. Southern blot of EcoRI-digested chromosomal DNAs of *L. monocytogenes* strains of different serotypes with Probe 1. Lanes 1 and 19, λ DNA digested with HindIII (fragment sizes, in kilobases are from top to bottom 23, 9.4, 6.5, 4.3, 2.3, 2.03, and 0.56); lanes 2–6, serotype 4b strains 4b1, M44, F4234, G3384, and G3622, respectively; lanes 7–8, serotypes 4a (ATCC 19114) and 4c (ATCC 19116), respectively; lanes 9–10, serotypes 4d (ATCC 19117) and 4e (ATCC 19118), respectively; lanes 11–15, serotypes 3a (ATCC 19113), 3b (SLCC2540), 3c (SLCC2479), 3c (G4315), and 7 (SLCC2480), respectively; lanes 16–18, serotype 1/2a strains G2228, Mack, and G3412, respectively.

DETAILED DESCRIPTION OF THE
PREFERRED EMBODIMENTS

I. Definitions

The terms "genomic cluster IIB sequence" when used herein encompasses *Listeria monocytogenes* native genomic cluster IIB sequence and variants (which are further defined herein). The genomic cluster IIB sequence may be isolated from a variety of sources, such as from *L. monocytogenes* genomic cluster IIB strains isolated from clinical samples or from compositions suspected of contamination or from another source, or prepared by recombinant and/or synthetic methods.

A "native genomic cluster IIB sequence" comprises a nucleic acid having the same nucleotide sequence as a genomic cluster IIB sequence derived from nature. Such native genomic cluster IIb sequences can be isolated from nature or can be produced by recombinant and/or synthetic means. The term "native genomic cluster IIB sequence" specifically encompasses naturally-occurring truncated forms and naturally-occurring variant forms (e.g., from different genomic cluster IIB species or strains). In one embodiment of the invention, the native genomic cluster IIB sequence is a full-length native sequence comprising nucleic acids 1 to 3060 of FIG. 5A (SEQ ID NO:1).

"Genomic cluster IIB variant" means a nucleic acid as defined below having at least about 80% nucleic acid sequence identity with the nucleic acid sequence of about residues 1 to about 3060 of the genomic cluster IIB sequence shown in FIG. 5A (SEQ ID NO:1). Such genomic cluster IIB variants include, for instance, genomic cluster IIB nucleic acids wherein one or more amino acid residues are added, deleted, or modified with respect to the sequence of FIG. 5A (SEQ ID NO:1). Ordinarily, a genomic cluster IIB sequence variant will have at least about 80% nucleic acid sequence identity, more preferably at least about 85% nucleic acid sequence identity, even more preferably at least about 90% nucleic acid sequence identity, and most preferably at least about 95% sequence identity with the nucleic acid sequence of about residues 1 to about 3060 of FIG. 5 (SEQ ID NO:1). Variants do not encompass the native sequence.

"Percent (%) nucleic acid sequence identity" with respect to the genomic cluster IIB sequence of *L. monocyotgenes* identified herein is defined as the percentage of nucleotide residues in a candidate sequence that are identical with the nucleotide residues in the genomic cluster IIB sequence, after aligning the sequences and introducing gaps, if necessary, to achieve the maximum percent sequence identity, and not considering any conservative substitutions as part of the sequence identity. The % identity values used herein were generated by the BLASTN module of WU-BLAST-2 which was obtained from [Altschul et al., *Methods in Enzymology,* 266: 460–480 (1996); http://blast.wustl/edu/blast/README.html] set to the default parameters, with overlap span and overlap fraction set to 1 and 0.125, respectively. A % nucleic acid sequence identity value is determined by the number of matching identical nucleotides divided by the total number of residues of the "longer" sequence in the aligned region. The "longer" sequence is the one having the most actual residues in the aligned region (gaps introduced by WU-Blast-2 to maximize the alignment score are ignored).

An "isolated" nucleic acid molecule comprising the various nucleic acids disclosed herein, means nucleic acid that has been identified and separated, recovered or liberated from a component of its natural environment. Contaminant components of its natural environment are materials that would typically interfere with the diagnostic or therapeutic uses for the nucleic acid, and may include enzymes, hormones, other proteinaceous or non-proteinaceous solutes, or other nucleic acids. In preferred embodiments, the nucleic acid will be purified to homogeneity by, for example, gel electrophoresis, chromatography, or centrifugation.

An isolated genomic cluster IIB nucleic acid molecule is other than in the form or setting in which it is found in nature. Isolated genomic cluster IIB nucleic acid molecules therefore are distinguished from the genomic cluster IIB nucleic acid molecule as it exists in natural cells. However, an isolated nucleic acid molecule comprising a genomic cluster IIB sequence includes genomic cluster IIB nucleic acid molecules contained in cells that ordinarily contain genomic cluster IIB nucleic acid, where, for example, the nucleic acid molecule is in a location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers single monoclonal antibodies (including agonist, antagonist, and neutralizing antibodies) and antibody compositions with polyepitopic specificity that recognize polypeptides and/or proteins encoded by the genomic cluster IIB sequences. The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and an explanation of stringency of hybridization reactions, see Ausubel et al., *Current Protocols in Molecular Biology,* Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual,* New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37–50° C. The skilled artisan will recognize how to adjust the temperature, ionic strength, etc. as necessary to accommodate factors such as probe length and the like.

II. Compositions and Methods of the Invention

A. *L. monocytogenes* Genomic Cluster IIB Nucleic Acids and Detection Methods

The present invention provides isolated nucleic acids encoding a serotype-specific nucleotide sequence of *Listeria monocytogenes* that is suitable for the detection and identification of strains most commonly associated with human disease. The serotype-specific nucleotide sequence from the *L. monocytogenes* chromosome is 3060 bp in length and encodes novel genes that are involved in the expression of unique surface antigens. The nucleotide sequence is unique to *L. monocytogenes* serovar 4 types 4b, 4d, and 4e, which make up genomic cluster IIB. Identification of serotype 4b is of practical interest because it is most commonly associated with human disease and serotypes 4d and 4e are virtually never isolated from patients. In general, the invention provides methods of identifying and detecting the presence of *L. monocytogenes* cluster IIB strains using nucleic acids that selectively hybridize and form detectable complexes with genomic cluster IIB nucleotide sequences.

The full-length native genomic cluster IIB sequence (SEQ ID NO:1) or fragments, thereof, may be used as hybridization probes to detect *L. monocytogenes* genomic cluster IIB strains and naturally-occurring variants which have a desired sequence identity to the genomic cluster IIB sequence disclosed in FIG. 5A (SEQ ID NO:1). Optionally, the length of the probe will be about 20 to about 50 bases. Probes of any length can be of sense or antisense polarity relative to SEQ ID NO:1. In one embodiment, the probe is labeled and forms a detectable complex with *L. monocytogenes* nucleic acid immobilized onto a solid support, such as, nitrocellulose, nylon membrane, or activated cellulose paper. After prehybridization to reduce non-specific hybridization, the solid support is hybridized under high stringency conditions to a nucleic acid probe of the invention. The solid support is washed to remove unbound and weakly binding probe, and the resulting hybrid duplex of probe and *L. monocytogenes* nucleic acid is detected. The *L. monocytogenes* target nucleic acid can be DNA, RNA or cDNA. Techniques to purify *L. monocytogenes* nucleic acids are described in Kathariou et al. *Infect. Immun.* 58:3988–3995 (1990) and methods to produce cDNA are described in Sambrook et al., *Molecular Cloning: A Laboratory Manual.* Cold Spring Harbor Laboratory Press. New York (1989).

To analyze DNA targets by Southern blotting, DNA fragments, commonly generated by restriction enzyme digestion, can be separated by agarose gel electrophoresis. Double stranded DNA is denatured in situ, for example, under alkaline conditions to disrupt base-pairing, thereby, permitting nucleic acid probes of the invention to hybridize with their target sequences. Alkaline denaturation is followed by neutralization and transfer to a solid support, such as, nitrocellulose or nylon membranes. Transfer from the gel to a solid support can be achieved by capillary, electrophoretic, or vaccum transfer. Following transfer, the support is prehybridized, probed, and examined for hybridized nucleic acid probe. The DNA fragments also can be fixed to nylon membranes by exposure to ultraviolet radition which causes the formation of covalent bonds between thymine residues and positively charged amino groups on the surface of the membrane. Alternatively, hybridization can be carried out in dried agarose gels. In this procedure, the agarose gel is dried and hybridization is carried out in situ using a nucleotide probe of the invention. This procedure may be preferable where speed of detection and sensitivity may be desirable.

RNA targets can be analyzed by Northern blotting. In this procedure, RNA is electrophoresed in agarose gels containing denaturants, such as glyoxal-dimethylsulfoxide or formaldehyde, to disrupt secondary structures. RNA can be transferred to solid supports, such as nitrocellulose or nylon membranes, by capillary, electrophoretic, or vaccum transfer. Following transfer, the support is prehybridizied, probed, and examined.

The *L. monocytogenes* nucleic acids also can be analyzed by dot blot or in situ hybridization of lysed bacterial colonies. For dot blot hybridization, the *L. monocytogenes* nucleic acid is treated with a denaturant and applied directly to the solid support which is dried, prehybridized, probed and examined as described above. For in situ hybridization bacterial colonies are lysed on solid supports, such as, nylon membranes, Whatman filter paper or nitrocellulose. The nucleic acids are immobilized and the solid supports are processed as described above.

The nucleic acid probes of the invention can be DNA or RNA and can be produced by chemical or enzymatic methods. For example, to produce RNA probes, the invention provides recombinant nucleic acids of *L. monocytogenes* genomic cluster IIB sequences. Nucleic acids encoding these sequences can be cloned into plasmid vectors and flanked by promoter sequences of DNA-dependent RNA polymerases, such as bacteriophage SP6, T3, or T7 RNA polymerase. RNA probes of sense or antisense polarity are produced by linearization of the vector downstream of the serotype-specific sequence followed by run-off transcription using the appropriate RNA polymerase. DNA probes of sense or antisense polarity can be produced by automated synthesis using, for example, an Applied Biosystems Oligonucleotide Synthesizer (Foster City, Calif.). A synthesis method can be chosen to produce, for example, DNA-RNA hybrid probes or probes with modified or non-phosphodiester backbones to enhance probe stability, enhance hybridization or to contain functional groups to facilitate detection or labeling. The polarity of the DNA or RNA probe is dependent on the nucleic acid target. For example, double-stranded chromosomal DNA hybridizes with sense and antisense probes whereas mRNA hybridizes with antisense probes.

The nucleic acid probes can be labeled with radioactive isotopes such as $^{32}P$, $^{32}H$, $^{14}C$, 125I, or $^{35}S$. Any radioactive label can be employed which provides an adequate signal and has sufficient half-life. Other types of labels include, for example, fluorescers, chemiluminescers, enzymes, antibodies which can specifically bind to a labeled ligand and the like. The nucleic acid probe also can be linked to biotin, which reacts with avidin which is labeled, rendering the hybrid DNA complex capable of being detected. The avidin can be labeled with, for example, a radioactive isotope, fluorescer, chemiluminescer, enzyme, antibody and the like as described above. The choice of label is governed by the effect of the label on the rate of hybridization and binding of the probe to the target nucleic acid. It will be necessary that the label provide sufficient sensitivity to detect the amount of *L monocytogenes* target nucleic acid available for hybridization. The rate of hybridization and binding is also dependent upon the stringency of the reaction conditions. In a preferred embodiment, the nucleic acid probes of the invention hybridize under high stringency conditions so as to minimize spurious hybridization.

The nucleotide sequences of the invention also can be employed to design oligonucleotide primers to identify and detect *L. monocytogenes* cluster IIB strains by the polymerase chain reaction (PCR). PCR is used to amplify a segment of DNA that lies beween two regions of known sequence. The oligonucleotide primer pairs specific for *L. monocytogenes* IIB strains are complementary to sequences that are found on opposite strands of the template DNA and flank the DNA segment to be amplified. Following multiple cycles of denaturation, annealing, and extension with a thermostable DNA polymerase a segment of double-stranded DNA is produced whose termini are defined by the 5'-termini of the oligonucleotide primers and whose length is defined by the distance between the primers. The reaction conditions for PCR are, generally, dependent upon primer length and composition, template concentration, the length of the DNA segment to be amplified, the properties of the thermostable DNA polymerase, and $Mg^{++}$ concentration. Each of these parameters is readily determinable by one of ordinary skill in the art in accordance with conventional practices.

In most instances, the amplified DNA is detected by agarose or acrylamide gel electrophoresis, ethidium bromide staining and UV irradiation. To increase the sensitivity of PCR or to decrease the number of cycles required to detect the amplification product, one or both of the oligonucleotide primers can be labeled as described above or a label can be incorporated into the amplified DNA during polymerization. To further increase sensitivity, nested PCR may be employed which uses a first set of primers followed by PCR with a second primer set that hybridizes to sequences internal to the first primer set.

The target DNA sequences to be amplified can be in single or double-stranded form. Double-stranded DNA are preferably linear because target sequences may be amplified less efficiently as a covalently closed circular form. Single-stranded cDNA produced by reverse transcription of mRNA also can be PCR amplified. cDNA can be produced by priming reverse transcriptase using oligo-dT that hybridizes to the poly(A) tail of mRNA or random primers, such as, random hexamers also can be used. Alternatively, a primer of the invention is used to prime reverse transcription followed by the addition of the second primer and PCR amplification.

The oligonucleotide probes and primers of the invention find use in the detection and identification of *L. monocytogenes* genomic cluster IIB strains. For example, by means of Southern blot or PCR, oligonucleotide probes and primers can be designed to unambiguously identify cluster IIB strains. This provides presumptive evidence of serotype 4b because it is the major component of this cluster, since other IIB strains, serotypes 4d and 4c, are isolated rarely from foods and virtually never from patients. In addition, the probes and primers of the invention allow the detection and identification of epidemic associated serotype 4b strains that may be difficult to type using antibody-based methodologies.

B. Expression of Polypeptides Encoded by *Listeria monocytogenes* Genomic Cluser IIB Nucleic Acids.

1. Selection and Transformation of Host Cells

Host cells are transfected or transformed with expression or cloning vectors described herein for production of polypeptides encoded by *Listeria monocytogenes* genomic cluster IIB and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of transfection are known to the ordinarily skilled artisan, for example, $CaPO_4$ and electroporation. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene*, 23:315 (1983) and WO 89/05859 published Jun. 29, 1989. For mammalian cells without such cell walls, the calcium phosphate precipitation method of Graham and van der Eb, *Virology*, 52:456–457 (1978) can be employed. General aspects of mammalian cell host system transformations have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci. (USA)*, 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527–537 (1990) and Mansour et al., *Nature*, 336:348–352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635).

In addition to prokaryotes, eukaryotic microbes such as filamentous fungi or yeast are suitable cloning or expression hosts for cluster IIB-encoding vectors. *Saccharomyces cerevisiae* is a commonly used lower eukaryotic host microorganism.

Suitable host cells for the expression of glycosylated polypeptides encoded by cluster IIB sequences are derived from multicellular organisms. Examples of invertebrate cells include insect cells such as Drosophila S2 and Spodoptera Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); Chinese hamster ovary cells/-DHFR (CHO, Urlaub and Chasin, *Proc. Natl. Acad. Sci. USA*, 77:4216 (1980)); mouse sertoli cells (TM4, Mather, *Biol. Reprod.*, 23:243–251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

2. Selection and Use of a Replicable Vector

The genomic cluster IIB nucleic acid (e.g., cDNA or genomic DNA) encoding genomic cluster IIB polypeptides may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The genomic cluster IIB encoded polypeptide may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the genomic cluster IIB polypeptide encoding sequence that is inserted into the vector. The signal sequence may be a prokaryotic signal sequence selected, for example, from the group of the alkaline phosphatase, penicillinase, 1 pp, or heat-stable enterotoxin II leaders. For yeast secretion the signal sequence may be, e.g., the yeast invertase leader, alpha factor leader (including Saccharomyces and Kluyveromyces α-factor leaders, the latter described in U.S. Pat. No. 5,010,182), or acid phosphatase leader, the *C. albicans* glucoamylase leader (EP 362,179 published Apr. 4, 1990), or the signal described in WO 90/13646 published Nov. 15, 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the $2\mu$ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the PRO240-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA,* 77:4216 (1980). A suitable selection gene for use in yeast is the trp1 gene present in the yeast plasmid YRp7 [Stinchcomb et al., *Nature,* 282:39 (1979); Kingsman et al., *Gene,* 7:141 (1979); Tschemper et al., *Gene,* 10:157 (1980)]. The trp1 gene provides a selection marker for a mutant strain of yeast lacking the ability to grow in tryptophan, for example, ATCC No. 44076 or PEP4-1 [Jones, *Genetics,* 85:12 (1977)].

Expression and cloning vectors usually contain a promoter operably linked to a genomic cluster IIB nucleic acid sequence to direct mRNA synthesis. Promoters recognized by a variety of potential host cells are well known. Promoters suitable for use with prokaryotic hosts include the β-lactamase and lactose promoter systems [Chang et al., *Nature,* 275:615 (1978); Goeddel et al., *Nature,* 281:544 (1979)], alkaline phosphatase, a tryptophan (trp) promoter system [Goeddel, *Nucleic Acids Res.,* 8:4057 (1980); EP 36,776], and hybrid promoters such as the tac promoter [deBoer et al., *Proc. Natl. Acad. Sci. USA,* 80:21–25 (1983)]. Promoters for use in bacterial systems also will contain a Shine-Dalgarno (S.D.) sequence operably linked to the DNA encoding genomic cluster IIB polypeptides.

Examples of suitable promoting sequences for use with yeast hosts include the promoters for 3-phosphoglycerate kinase [Hitzeman et al., *J. Biol. Chem.,* 255:2073 (1980)] or other glycolytic enzymes [Hess et al., *J. Adv. Enzyme Reg.,* 7:149 (1968); Holland, *Biochemistry,* 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Transcription from vectors in mammalian host cells is controlled, for example, by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding a genomic cluster IIB polypeptide by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. The enhancer may be spliced into the vector at a position 5' or 3' to the genomic cluster IIB polypeptide coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding genomic cluster IIB polypeptides.

Still other methods, vectors, and host cells suitable for adaptation to the synthesis of genomic cluster IIB polypeptides in recombinant vertebrate cell culture are described in Gething et al., *Nature,* 293:620–625 (1981); Mantei et al., *Nature,* 281:40–46 (1979); EP 117,060; and EP 117,058.

C. Anti-*Listeria monocytogenes* Genomic Cluster IIB Antibodies

The present invention further provides anti-genomic cluster IIB polypeptide antibodies. Exemplary antibodies include polyclonal, monoclonal, humanized, bispecific, and heteroconjugate antibodies.

1. Polyclonal Antibodies

The anti-cluster IIB antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include a cluster IIB polypeptide, or fragment or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-cluster IIB antibodies may, alternatively, be monoclonal antibodies. Monoclonal antibodies may be prepared using hybridoma methods, such as those described by Kohler and Milstein, *Nature,* 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include a genomic cluster IIB polypeptide or fragment or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51–63].

The culture medium in which the hybridoma cells are cultured can then be assayed for the presence of monoclonal antibodies directed against an immunizing cluster IIB polypeptide. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

3. Human and Humanized Antibodies

The anti-genomic cluster IIB antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522–525 (1986); Riechmann et al., *Nature*, 332:323–329 (1988); and Presta, *Curr. Op. Struct. Biol.*, 2:593–596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522–525 (1986); Riechmann et al., *Nature*, 332:323–327 (1988); Verhoeyen et al., *Science*, 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.*, 227:381 (1991); Marks et al., *J. Mol. Biol.*, 222:581 (1991)]. The techniques of Cole et al. and Boerner et al. are also available for the preparation of human monoclonal antibodies (Cole et al., *Monoclonal Antibodies and Cancer Therapy,* Alan R. Liss, p. 77 (1985) and Boerner et al., *J. Immunol.,* 147(1):86–95 (1991)]. Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10, 779–783 (1992); Lonberg et al., *Nature* 368 856–859 (1994); Morrison, *Nature* 368, 812–13 (1994); Fishwild et al., *Nature Biotechnology* 14, 845–51 (1996); Neuberger, *Nature Biotechnology* 14, 826 (1996); Lonberg and Huszar, *Intern. Rev. Immunol.* 13 65–93 (1995).

4. Bispecific Antibodies

Bispecific antibodies are monoclonal, preferably human or humanized, antibodies that have binding specificities for at least two different antigens. In the present case, one of the binding specificities is for a polypeptide encoded by genomic cluster IIB sequences, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, *Nature,* 305:537–539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., *EMBO J.,* 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology,* 121:210 (1986).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

D. Uses for *Listeria monocytogenes* Anti-genomic Cluster IIB Antibodies

The anti-genomic cluster IIB antibodies of the invention have various utilities. For example, anti-genomic cluster IIB antibodies may be used in diagnostic assays for *L. monocytogenes* cluster IIB strains, e.g., detecting their presence in clinical samples or food suspected of being contaminated. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques,* CRC Press, Inc. (1987) pp. 147–158]. The antibodies used in the diagnostic assays can be labeled with a detectable moiety. The detectable moiety should be capable of producing, either directly or indirectly, a detectable signal. For example, the detectable moiety may be a radioisotope, such as $^{3}H$, $^{14}C$, $^{32}P$, 35S, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature,* 144:945 (1962); David et al., *Biochemistry,* 13:1014 (1974); Pain et al., *J. Immunol. Meth.,* 40:219 (1981); and Nygren, *J. Histochem. and Cytochem.,* 30:407 (1982).

Anti-cluster IIB antibodies also are useful for the affinity purification of cluster IIB encoded polypeptides from recombinant cell culture or natural sources. In this process, the antibodies against cluster IIB polypeptides are immobilized on a suitable support, such a Sephadex resin or filter paper, using methods well known in the art. The immobilized antibody then is contacted with a sample containing the cluster IIB polypeptide to be purified, and thereafter the support is washed with a suitable solvent that will remove substantially all the material in the sample except the cluster IIB, which is bound to the immobilized antibody. Finally, the support is washed with another suitable solvent that will release the cluster IIB polypeptide from the antibody.

The following examples are offered for illustrative purposes only, and are not intended to limit the scope of the present invention in any way.

All patent and literature references cited in the present specification are hereby incorporated by reference in their entirety.

EXAMPLES

Example 1

Mapping the Genomic Regions of *Listeria monocytogenes* Involved in the Expression of Cluster IIB-specific Antigens.

Transposon mutagenesis was performed to map the genomic regions of *L. monocytogenes* involved in the expression of cluster IIB-specific antigens. MAbs c74.22 and c74.33 were previously shown to react specifically with strains of serotypes 4b, 4d, and 4e (i.e. genomic cluster IIB) (Lei et al., 1994. Appl. Environ. Microbiol. 60:3548–3552). The genomic regions involved in the expression of the antigens recognized by these MAbs were identified by the analysis of mutants that lost reactivity with at least one of these Mabs that were generated by the insertion of transposons Tn916 or Tn916ΔE into the bacterial genome. Transposon mutagenesis was performed by filter matings using serotype 4b strains 4b1 and 2381 L (streptomycin-resistant derivatives of strains NCTC 10527 and F2381, respectively) as described by Zheng and Katharious. 1994. FEMS Microbiol. Lett. 121:287–292. Tn916 and Tn916ΔE encode for tetracylcine and erythromycin resistance, respectively, allowing mutants to be isolated by their acquisition of resistance to each antibiotic.

Isolated transconjugants were inoculated into individual wells of 96-well culture plates containing 200 μl of brain heart infusion broth with streptomycin and either tetracyline or erythromycin. The 96-well plates were incubated at 37° C. overnight and were subsequently frozen at −70° C. The mutants from the 96-well plates stored at −70° C. were inoculated with a 48-prong replicating device on Tryptic Soy Broth—0.7% Yeast Extract—1.2% Agar Plates with appropriate antibiotics and

TABLE I

Listeria strains and Southern Blot Detection Results

| | | Hybridization with probe: | |
|---|---|---|---|
| Species and Strain | Serotype | 1[a] | 2[b] |
| *L. monocytogenes* | | | |
| 4b1 | 4b | + | + |
| M44[c] (Tn916ΔE mutant) | 4b | + | +[c] |
| XL1[c] (Tn916 mutant) | 4b | + | +[c] |
| XL12[c] (Tn916ΔE mutant) | 4b | + | +[c] |
| XL3[c] (Tn916 mutant) | 4b | + | +[c] |
| XL7[d] (Tn916ΔE mutant) | 4b | +[f] | + |
| XL8[d] (Tn916ΔE mutant) | 4b | +[f] | + |
| XL9[d] (Tn916ΔE mutant) | 4b | +[f] | + |
| XL10[d] (Tn916ΔE mutant) | 4b | +[f] | + |
| XL11[d] (Tn916ΔE mutant) | 4b | +[f] | + |
| XL12[d] (Tn916ΔE mutant) | 4b | +[f] | + |
| F4234 | 4b | + | + |
| F4243 | 4b | + | + |
| F4244 | 4b | + | + |
| F4258 | 4b | + | + |
| G3384 | 4b | + | + |
| G3622 | 4b | + | + |
| G3680 | 4b | + | + |
| 1849A | 4b | + | + |
| 18 | 4b | + | + |
| 15U | 4b | + | + |
| 2202 | 4b | + | + |
| 2211 | 4b | + | + |
| 2212 | 4b | + | + |
| 2381L | 4b | + | + |
| 33 | 4b | + | + |
| G2228 | 1/2a | − | − |
| G2294 | 1/2a | − | − |
| G3412 | 1/2a | − | − |
| G4313 | 1/2a | − | − |
| Mack | 1/2a | − | − |
| UN27 | 1/2a | − | − |
| F4236 | 112b | − | − |
| F4242 | 1/2b | − | − |
| F4245 | 1/2b | − | − |
| F4260 | 1/2b | − | − |
| G4233 | 1/2b | − | − |
| G4312 | 1/2b | − | − |
| LM103 | 1/2c | − | − |
| ATCC 19113 | 3a | − | − |
| SLCC2540 | 3b | − | − |
| G3331 | 3b | − | − |
| G3443 | 3c | − | − |
| G4315 | 3c | − | − |
| SLCC2479 | 3c | − | − |
| ATCC 19114 | 4a | − | + |
| ATCC 19116 | 4c | − | + |
| ATCC 19117 | 4d | + | + |
| ATCC 19118 | 4e | + | + |
| SLCC2480 | 7 | − | − |
| 2632 | ND[g] | − | − |
| 2422 | ND[g] | − | − |
| *L. ivanovii* | | − | − |
| *L. welshimeri* | | − | − |
| *L. grayi* | | − | − |
| *L. seeligeri* | | − | − |
| *L. innocua* | | − | − |
| F7833 | | +[h] | + |
| F8596 | | +[h] | + |
| F8735 | | +[h] | + |
| 120A1 | | − | − |
| 121E9 | | − | − |
| 29M1 | | − | − |
| 30L1 | | − | − |
| 31L1 | | − | − |

[a]Hybridizing EcoRI fragments were 4.5 kb in epidemic-associated strains and either 4.5 or 5.0 kb in other serotype 4b strains.
[b]Hybridizing EcoRI fragment was 0.8 kb.
[c]Mutant was MAb c 74.22 negative but MAb c74.33 positive.
[d]Mutant was negative with both MAbs c74.22 and c74.33.
[e]Hybridizing EcoRI fragment was ca. 19 kb (with Tn916ΔE)
[f]Hybridizing EcoRI fragment was ca, 23 kb (with Tn916ΔE)
[g]ND, not determined. Strains 2362 (an environmental isolate from a dairy plant) and 2422 (a raw milk isolated) lacked serotype 4b-specific surface antigens and are likely not serotype 4b.
[h]Hybridizing EcoRI fragment was ca. 2.2 kb.

grown overnight at 22° C. Bacterial colonies were transferred onto nitrocellulose membranes (Micron Separations Inc.) presoaked in Towbin transfer buffer (Ausbel et al. Current Protocols in Molecular Biology. Green Publishing Associates and John Wiley and Sons, Inc. New York, N.Y.). The nitrocellulose membranes were air dried for 15 min. and processed according to standard immunoblot procedures (Kathariou et al. 1994. Appl. Environ. Microbiol. 60:3548–3552). MAbs c74.22 and c74.33 were used as ascites at a 1:400 dilution. MAb binding was demonstrated using goat antimouse-horseradish peroxidase conjugate (1:1000 dilution; Fisher).

Of the 10,464 transposon mutants analyzed, three mutants (XL-1, XL-2, and XL-3) lost reactivity with c74.22 (c74.22-negative) but retained reactivity with c74.33 (c74.33-positive) and six mutants (XL-4, XL-5, XL-6, XL-7, XL-8, and XL-9) were c74.22-negative and c74.33-negative (Table 1). An additional c74.22-negative/c74.33-positive mutant, M44, had been previously identified (Kathariou et al. 1994. Appl. Environ. Microbiol. 60:3548–3552; Promadej and Kathariou. Abstr. B-154. In Abstracts of 93rd General Meeting of the American Society for Microbiology 1993. AMS, Washington, DC).

To unambiguously map the insertion site of the transposons and map the genomic regions involved in cluster-IIB-specific antigen expression, mutants containing a single transposon copy were identified for further analysis. The number of transposon copies in each mutant was determined by Southern blots using a digoxigenin-labeled Tn916 probe. Tn916 and Tn916ΔE each have a single internal HindIII site and, therefore, blots of HindIII-digested chromosomal DNA from single-transposon mutants probed with transposon sequences will reveal only two hybridizing bands.

Listeria genomic DNA was extracted as previously described (Kathariou et al. 1990. Infect. Immun. 58:3988–3995) from 4.5 ml of culture grown for about 18 hours at 37° C. in brain heart infusion broth (Difco), with the modification that a hexadecyl trimethyl ammonium bromide extraction step was included (Ausubel et al. (ed.) 1987.

Current protocols in molecular biology. Greene Publishing Associates and John Wiley & Sons, Inc., New York, N.Y.). Chromosomal DNA corresponding to 0.25–0.5 ml of culture was restriction enzyme digested according to the manufacturer's protocols (Promega) and used for Southern blots. Non-radioactive labelled probes were generated with the digoxigenin-based Genius kit (Boehringer-Mannhein). The results showed that mutants M44, XL7, and XL8 have a single copy of Tn916ΔE and that mutant XL3 had a single copy of Tn916. Tn916ΔE mutants, M44 and XL7, were chosen for further analysis.

DNA fragments of 1.1 and 0.6 kb flanking the transposon insertions in XL7 and M44, respectively, were amplified by single-specific primer PCR and cloned in pCR1000. Chromosomal DNA from XL7 and M44 was EcoRI digested and ligated into EcoRI-digested and dephosphorylated vectors: pCR1000 (Invitrogen) and M13Mp18RF (Pharmacia). Single-specific primer PCR (Shyamala and Ames. 1989. Gene 84:1–8) was performed using the transposon-specific primer OTL (5'-CGGAATTCCGTGAAGTATCTTCCTACAG-3'; SEQ ID NO:6) with an EcoRI recognition sequence (underlined) at the 5' end and the M13 reverse primers (5'-CAGGAAACAGCTATGACCATGATT-3'; SEQ ID NO:7). The PCR product was purified by extraction from low-melting-point agarose (Amresco) as previously described (Ausubel et al., supra.), EcoRI digested and cloned in pCR1000.

Southern blots using the pCR1000 cloned fragments as probes confirmed that the fragments flanked on one side of the transposon in their respective mutants and that M44 and XL7 harbored transposon insertions in different genomic regions separated by at least 5 kb (data not shown). Furthermore, blots revealed that mutant XL7, as well as four other, independently isolated mutants of the same phenotype, carried a transposon insertion in a 5.0 kb, EcoRI fragment (FIG. 1A). M44, on the other hand, as well as three other, independently isolated mutants of the same phenotype, carried a transposon in a 0.8-kb EcoRI fragment (FIG. 1B). These data suggest that the phenotypes of the mutants were associated with the transposon insertion and were not a result of an unrelated genetic lesion (e.g., spontaneous muation). The 1.1-kb DNA fragment flanking the transposon insertion in mutant XL7 was cloned in PCR1000, yielding the recombinant plasmid pXL7-1 (FIG. 1A), which was used as a digoxigenin-labeled probe (Probe 1) in Southern blots and DNA dot blots. A 0.3-kb DNA fragment internal to the 0.6-kb transposon-flanking fragment from M44 (FIG. 1B) was obtained as previously described (Lei et al. 1995. In M. Eklund, J. L. Richard, K. Mise (ed.), Molecular Approaches to Food Safety: Issues Involving Toxic Microorganisms. pp. 417–25. Alaken, Inc. Denver, Colo.) and was also used as a digoxigenin-labeled probe (Probe 2) in Southern blots.

Example 2

Genomic Regions of *Listeria monocytogenes* Involved in Cluster IIB-specific Antigen Expression are Present Only in Serotype 4b, 4d and 4e This experiment was performed to identify that the genomic regions that are present only in serotypes 4b, 4d, and 4e.

Figure 3:
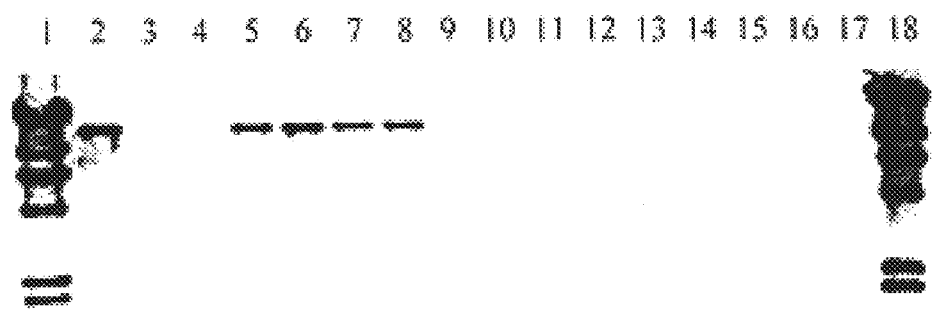
FIG. 3. Southern blot of HindIII-digested chromosomal DNAs from various serotypes of *L. monocytogenes* and other Listeria species with Probe 1. Lanes 1 and 18, λ molecular markers (see FIG. 2); lanes 2–12, F4244 (4b); F4260 (1/2b), G4233 (1/2b), 2381L (4b), 15U (4b), 18 (4b), Mack (1/2a), G2228 (1/2a), G2294 (1/2a), and G4312 (1/2b), respectively; lanes 13–17, other Listeria species (*L. grayi, L. welshimeri, L. seeligeri, L. innocua* [strain 120A1], and *L. invanovii,* respectively).

EcoRI and/or HindIII digested chromosomal DNA of *L. monocytogenes* strains of serotypes 4b, 4a, 4c, 4d, 4e, 3a, 3b, 3c, 1/2a, 1/2b, 1/2c, and 7 were examined by Southern blot with Probe 1 and Probe 2. Serovar 4 strains (4a, 4b, 4c, 4d, 4e) hybridized with Probe 2 but only genomic cluster IIB strains (4b, 4d, 4e) hybridized to Probe 1. Strains representing the other *L. monocytogenes* serotypes (1/2a, 1/2b, 1/2c, 3a, 3b, 3c, and 7) did not hybridize to either probe (FIGS. 2 and 3, Table 2). All serotype 4b strains showed a strong hybridizing band corresponding to an EcoRI fragment of approximately 4.5–5.0 kb (FIG. 2, Table 1) or a large HindIII fragment of approximately 20 kb (FIG. 3, Table 1). The difference in the size of the hybridizing EcoRI fragments was small but was consistently observed and may reflect an EcoRI site polymorphism in this region.

The strains of an epidemic-associated isolate (Bibb et al. 1990. Appl. Environ. Microbiol. 56:2133–2141, Bibb et al. 1989. Int. J. Food Microbiol. 8:233–239, Piffaretti et al. 1989. Proc. Natl. Acad. Sci. USA 86:3818–3822, Zheng and Katharious. 1995. Appl. Environ. Microbiol. 61 "4310–4314) had a 4.5-kb hybridizing EcoRI band (data not shown), whereas other serotype 4b strains had either 4.5- or 5.0-kb bands (FIG. 2). Serotype 4b strains yielded a 0.8-kb EcoRI hybridizing fragment in Southern blots with Probe 2 (Table 1) but no restriction fragment length polymorphism (RFLP) was detected.

TABLE 2

Reactivity Patterns of *L. monocytogenes* with MAbs and DNA Probes

| | Reactivity pattern for: | | | | | |
|---|---|---|---|---|---|---|
| | Serovar 4 | | | | | |
| | Cluster IIB | | | Other | | |
| MAb or Probe | 4b | 4d | 4e | 4a | 4c | Other serovars[a] |
| MAb c74.22 | + | + | + | − | − | − |
| MAb c74.33 | + | + | + | − | − | − |
| Probe 1 | + | + | + | − | − | − |
| Probe 2 | + | + | + | + | + | − |

[a]Serovars 1/2a, 1/2b, 1/2c, 3a, 3b, 3c, and 7)

Example 3

Dot-Blot Hybridization of *Listeria monocytogenes* Chromosomal DNA

Figure 4:
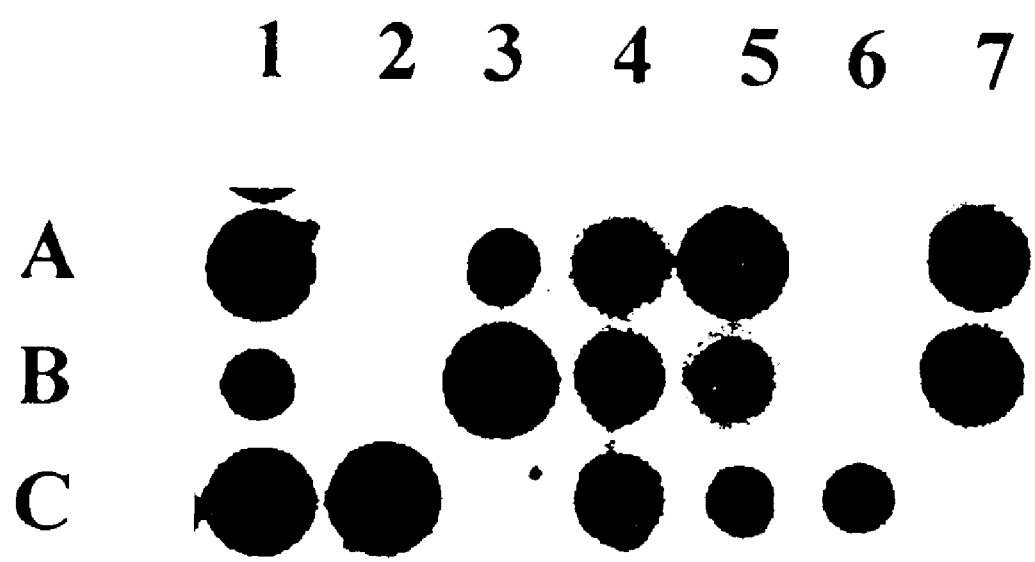
FIG. 4. Dot blot of chromosomal DNA of Listeria species with Probe 1. Hybridization was observed with all serotype 4b strains: strains 2201, 2204, 2205, 2206, and 2207 (spots A1, A3–A5, A7, respectively); strains 2209, 2210, 2213, 2214, and 2215 (spots B1, B3–B5, and B7, respectively); strains 2217, 2218, 2220, 2222, and 2223 (spots C1, C2, and C4–C6, respectively). Serotype 4b strains were from a Nova Scotia outbreak (Schuchat et al. 1991. Clin. Microbiol. Rev. 4:169–183). No hybridization was seen with SLCC2480 (serotype 7, spot A2), G2228 (1/2a, spot A6), G3412 (1/2a, spot B2), *L ivanovii* (spot B6); and two non-serotype 4b strains (2362 and 2422, spots C3 and C7, respectively). Variation in signal intensity may reflect differences in DNA concentration of the samples.

The specificity of Probe 1 was examined by dot-blot hybridization of *L. monocytogenes* chromosomal DNA of serotype 4b (strains 2201, 2204, 2205, 2206, 2207, 2209, 2210, 2213, 2214, 2215, 2217, 2218, 2220, 2222, 2223), serotype 1/2a (strains G2228, G3412), and serotype 7 (strain SLCC2480). Included in this analysis were two strains of unknown serotype, 2362 and 2422. Genomic DNA corresponding to 0.05 to 0.01 ml of culture was used for hybridization with Probe 1. The results, shown in FIG. 4, demonstrate that Probe 1 hybridized to each serotype 4b strain examined but not to strains of serotypes 1/2a, 7, or strains of an unknown serotype.

Example 4

Probes 1 and 2 Hybridize to Chromosomal DNA of *L. monocytogenes* Serotype 4b Field Isolates that are c74.22-negative/c74.33-positive This experiment was performed to determine if Probes 1 and 2 can be used to identify serotype 4b field isolates that do not react with MAb c74.22 but retain reactivity with c74.33. Strains 18, 15U, and 2202 are epidemic-associated serotype 4b strains that were previously shown to be c74.22- negative/c74.33-positive (Kathariou et al. 1994. Appl. Environ. Microbiol. 60:3548–3552). The genetic basis for the unique antigenic profile or these strains has not been conclusively determined but the data suggest that these strains lack the surface antigen recognized by c74.22. However, despite the absence of the c74.22 reactive antigen, both Probes 1 and 2 reacted normally with these strains (Table 1).

Example 5

Reactivity of Probes 1 and 2 with other Listeria Species

Probes 1 and 2 did not hybridize with chromosomal DNA of *L. ivanovii, L. welshimeri, L. seeligeri,* and *L. grayi* (Table 1). However, three of eight strains of *L. innocua* (F7833, F8596, and F8735), previously shown to react with MAbs c7422 and c74.33 (Katharious et al. 1994. Appl. Environ. Micrbiol. 60:3548–3552) hybridized with both probes. In a Southern blot, Probe 1 hybridized to a 2.2 kb, EcoRI fragment which is significantly smaller that the 4.5–5.0-kb fragment identified in *L. monocytogenes* cluster IIB strains. With Probe 2, *L. innocua* strains F7833, F8596, and F8735, revealed a 0.8-kb hybridizing EcoRI fragment (Table 1) which is similar to the fragment identified with *L. monocytogenes* serovar 4 strains. Other *L. innocua* strains did not reactive with either probe (Table 1).

Example 6

Cloning and Nucleotide Sequence of the Genomic Region of *Listeria monocytogenes* Unique to Cluster IIB Strains One of the Tn916 mutants that lacked reactivity with MAbs c74.22 and c74.33 was used to clone a region of *L. monocytogenes* genome that was unique to genomic cluster IIB strains. Using a single-specific-primer PCR (one primer was designed based on Tn916 and the other was the universal M13 reverse primer, a region of *L. monocytogenes* serotype 4b genomic DNA fragment flanking the transposon was amplified. The PCR was performed with Expand High Fidelity PCR System (Boehringer Mannheim). The reverse PCR products were directly cloned into the TA cloning vector (Invitrogen). The insert was sequenced in its entirety by the Sanger dideoxy chain termination method. In some instances, uncloned PCR products were sequenced to resolve ambiguities and to arrive at a consensus.

The nucleotide sequence of the insert was used to query DNA databases using the GCG and BLAST algorithm default settings. The searches did not identify a nucleotide sequence that shared statistically significant identity with the SEQ ID NO:1, indicating that it is unique to *L. monocytogenes* genomic cluster IIB strains.

The derived sequence, shown in FIG. 5A (SEQ ID NO:1), is 3060 bases in length and encodes two open reading frames: ORF-1 from nucleotides 374–2020 and ORF-2 from nucleotides 2031–2978. Comparison of this sequence with the results of the transposon mutagenesis analysis and Southern blots described above indicates that that ORF-1 and -2 are involved in the expression of the epitopes recognized by MAbs c74.22 and c74.33, respectively. The deduced amino acid sequences of ORF-1 (SEQ ID NO:4) and -2 (SEQ ID NO:5) are shown in FIG. 5B.

Example 7

Figure 6:
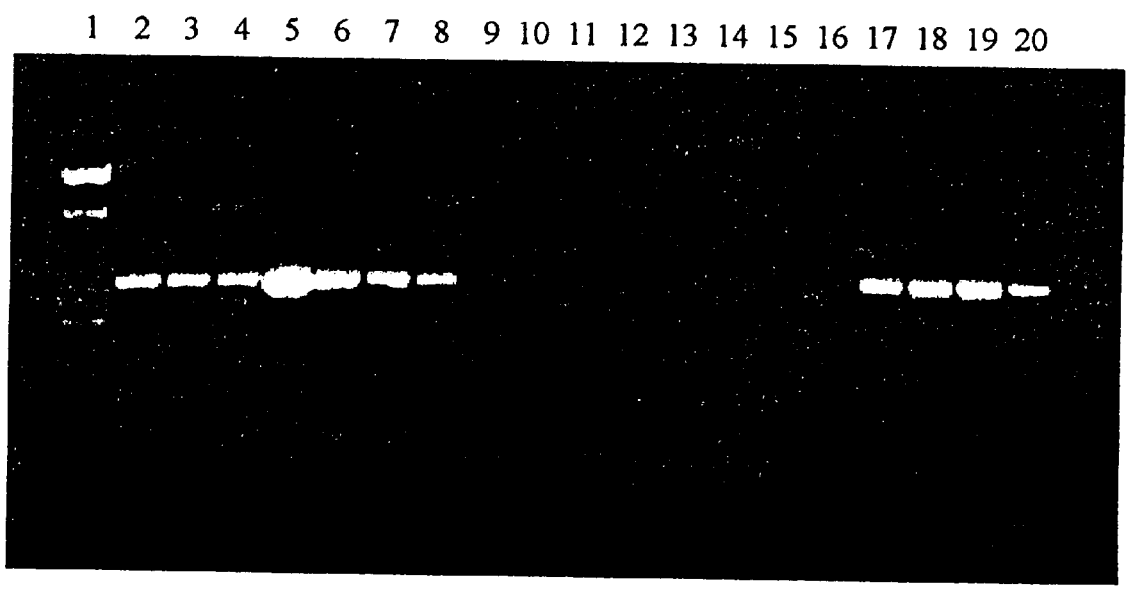
FIG. 6. Electrophoresis of PCR products amplified from Listeria chromosomal DNAs of different species and/or serotypes. The primers PR1 and PR2 derived from locus II of *L. monocytogenes* serotype 4b strain 4b1. The bands show an 853 base pair DNA fragment. Lane 1: 100 bp DNA ladder. Lanes 2–8 and 17–20: *L. monocytogenes* serotype 4b strains: 4b1, XL7, M44, F2381, 15u, 18, 2202, 2211, F4234, F4243, and F4244, respectively. Lanes 9–14: *L. monocytogenes* serotypes 4a, 4c, 4ab (F2940), 4c (ATCC19116), 1/2a (Mack), 1/2b (F4236), respectively. Lane 15: *L. ivanovii.* Lane 16: *L. welshimeri.*

Identification of *Listeria monocytogenes* Genes Genomic Cluster IIB Strains by PCR Chromosomal DNA of *L. monocytogenes* serotype 4b strains 4b1, XL7, M44, F2381, 15u, 18, 2202, 2211, F4234, F4243, F4244, serotypes 4a, 4c, 4ab, 4c, 1/2a, 1/2b and *L. ivanovii,* and *L welshimeri* were purified as described above and PCR amplified using primers P1 (5'-TCATCGTATCGCTTCTGTG; SEQ ID NO:2) and P2 (5'-GTGCCATTACTACAGGTGCA; SEQ ID NO:3) and Taq polymerase (Perkin-Elmer). Primers P1 and P2 correspond to nucleotides 1047–1065 and nucleotides 1879–1897 of SEQ ID NO:1. The profile of each amplification cycle was: 1 min. at 90° C., 1 min. at 50° C., 2 min. at 70° C. (30 cycles). The PCR products were analyzed by agarose gel electrophoresis and ethidium bromide staining. The results, shown in FIG. 6, indicate that primers PR1 and PR2 amplified a 851 bp product from all *L. monocytogenes* serotype 4b strains tested and were negative with other *L. monocytogenes* serotypes, *L ivanovii,* and *L. welshimeri.* Primers P1 and P2 also amplified a 851 bp product from *L. monocytogenes* serotypes 4d and 4e (data not shown) and are therefore specific for genomic cluster IIB strains.

CONCLUDING REMARKS

The foregoing description details specific methods which can be employed to practice the present invention. Having detailed such specific methods, those skilled in the art will well enough know how to devise alternative reliable methods at arriving at the same information in using the fruits of the present invention. Thus. however detailed the foregoing may appear in text, it should not be construed as limiting the overall scope thereof; rather, the ambit of the present invention is to be determined only by the lawful construction of the appended claims. All documents cited herein are hereby expressly incorporated by reference.

REFERENCES

1. Ausubel, F. M., R. Brent, R. E. Kingston, D. D. Moore, J. G. Seidmann, J. A. Smith and K. Struhl (ed.). 1987. *Current protocols in molecular biology.* Greene Publishing Associates and John Wiley & Sons, Inc., New York, N.Y.
2. Bhunia, A. K. and M. G. Johnson. 1992. Monoclonal antibody specific for *Listeria monocytogenes* associated with a 66-kilodalton cell surface antigen. *Appl. Environ. Microbiol.* 58:1924–1929.
3. Bibb, W. F., B. G. Gellin, R. Weaver, B. Schwartz, B. D. Plikaytis, M. W. Reeves, R. W. Pinner and C. V. Broome. 1990. Analysis of clinical and food-borne isolates of *Listeria monocytogenes* in the United Stats by multilocus enzyme electrophoresis and application of the method to epidemiological investigations. *Appl. Environ. Microbiol.* 56:2133–2141.
4. Bibb, W. F., B. Schwartz, B. G. Gellin, B. D. Plikaytis and R. E. Weaver. 1989. Analysis of *L. monocytogenes* by multilocus enzyme electrophoresis and application of the method to epidemiologic investigations. *Int. J. Food Microbiol.* 8:233–239.
5. Brosch, R., J. Chen and J. B. Luchansky. 1994. Pulsed-field fingerprinting of Listeriae: identification of genomic divisions for *Listeria monocytogenes* and their correlation with serovar. *Appl. Environ. Microbiol.* 60:2584–2592.
6. Chen, J., R. Brosch and J. B. Luchansky. 1993. Isolation and characterization of *Listeria monocytogenes*-specific nucleotide sequences. *Appl. Environ. Microbiol.* 59:4367–4370.
7. Clewell, D. B., S. E. Flannagan, Y. Ike, J. M. Jones and C. Gawron-Burke, 1988. Sequence analysis of termini of conjugative transposon Tn916. *J. Bacteriol.* 170:3046–3052.
8. Czajka, J., N. Bsat, M. Piani, W. Russ, K. Sultana, M. Wiedman, R. Whitaker and C. A. Batt. 1993. Differentiation of *Listeria monocytogenes* and *Listeria innocua* by 16S rRNA and intraspecies discrimination of *Listeria monocytogenes* strains by random amplified polymorphic DNA polymorphisms. *Appl. Environ. Microbiol.* 59:304–308.

9. Ericsson, H., P. Stalhandske, M. L. Danielsson-Tham, E. Bannerman, J. Bille, C. Jacquet, J. Rocourt and W. Tham. 1995. Division of *Listeria monocytogenes* serovar 4b strains into two groups by PCR and restriction enzyme analysis. *Appl. Environ. Microbiol.* 61:3872–3874.

10. Farber, J. M. and P. L. Peterkin. 1991. *Listeria monocytogenes*, a food-borne pathogen. *Microbiol. Rev.* 55:476–511.

11. Kathariou, S., L. Pine, V. George, G. M. Carlone and B. P. Holloway. 1990. Nonhemolytic *Listeria monocytogenes* mutants that are also noninvasive for mammalian cells in culture: evidence for coordinate regulation of virulence. *Infect. Immun.* 58:3988–3995.

12. Kathariou, S., C. Mizumoto, R. D. Allen, A. K. Fok and A. A. Benedict. 1994. Monoclonal antibodies with a high degree of specificity for *Listeria monocytogenes* serotype 4b. *Appl. Environ. Microbiol.* 60:3548–3552.

13. Lei, X. -H., N. Promadej, F. Fielder and S. Kathariou. 1995. Serotype surface antigens of *Listeria monocytogenes*, abstr. D-18, p.251. In Abstracts of the 95th General Meeting of the American Society for Microbiology 1995. *American Society for Microbiology*, Washington, D.C.

14. Lei, X. -H., N. Promadej, W. Zheng and S. Kathariou. 1995. Cell surface antigenic composition and low temperature growth of *Listeria monocytogenes* serotype 4b, p. 417–425. In M. Eklund, J. L. Richard and K. Mise (ed.), Molecular approaches to food safety: issues involving toxic microorganism. Alaken, Inc. Denver, Colo.

15. Lei, X. -H., N. Promadej and S. Kathariou. Unpublished data.

16. Piffaretti, J. C., H. Kressebuch, M. Aeschbacher, J. Bille, E. Banneraman, J. M. Musser, R. K. Selander and J. Rocourt. 1989. Genetic characterization of clones of the bacterium *L. monocytogenes* causing epidemic disease. *Proc. Natl. Acad. Sci. USA* 86:3818–3822.

17. Promadej, H. and S. Kathariou. 1993. A transposon-induced *Listeria monocytogenes* mutant which is deficient in invasion of murine fibroblasts, abstr. B-154, p. 53. In Abstracts of the 93rd General Meeting of the American Society for Microbiology 1993. *American Society for Microbiology*, Washington D.C.

18. Schoenberg, A., P. Teufel and E. Weise. 1989. Serovars of *Listeria monocytogenes* and *L. innocua* from food. *Acta Microbiol.* Hung. 36:249–253.

19. Schucat, A., B. Swaminathan and C. V. Broome. 1991. Epidemiology of human listeriosis. *Clin. Microbiol. Rev.* 4:169–183.

20. Seeliger, H. P. R., and K. Höhne. 1979. Serotype of *Listeria monocytogenes* and related species. *Methods Microbiol.* 13:31–49.

21. Shyamala, V. and G. Ferro-Luzzi Ames. 1989. Genome walking by single-specific primer polymerase chain reaction:SSP-PCR. gene 84:1–8.

22. Tabouret, M., J. De Rycke and G. Dubray. 1992. Analysis of surface proteins of Listeria in relation to species, serovar and pathogenicity. *J. Gen. Microbiol.* 138:743–753.

23. Walker, S. J., P. Archer and J. G. Banks. 1990. Growth of *Listeria monocytogenes* at refrigeration temperatures. *J. Appl. Bacteriol.* 68:157–162.

24. Zheng, W. and S. Kathariou. 1994. Transposon-induced mutants of *Listeria monocytogenes* incapable of growth at low temperature (4° C.). *FEMS Microbiol. Lett.* 121:287–292.

25. Zhen, W. and S. Kathariou. 1995. Differentiation of epidemic-associated strains of *Listeria monocytogenes* by restriction fragment length polymorphism in a gene region essential for growth at low temperature (4° C.). *Appl. Environ. Microbiol.* 61:4310–4314.

26. Bjerklie, David. "The Dangers of Foul Fowl," *Time*, Vol. 136, Nov. 26, 1990, p. 78.

27. "Preventing Foodborne Listeriosis." vm.cfsan.fda.gov/~fsis/FSISLIST.html

28. "Preventing Foodborne Illness: Listeriosis." www.cdc.gov/ncidod/diseases/foodborn/lister.htm 29. "PRO/AH>*Listeria monocytogenes* (GIDEON)." www.healthnet.org/programs/promed-hma/9708/msg00184.html 30. Wagner, Al B. Jr. "Bacterial Food Poisoning." aggie-horticulture.tamu.edu/extensio/poinson.html 31. U. S. Food & Drug Administration Center for Food Safety & Applied Nutrition. "Foodborne Pathogenic Microorganisms and Natural Toxins," 1992. (Bad Bug Book). www,cfsan.fda.gov/~mow/chap6.html

What is claimed is:

1. An isolated nucleic acid molecule that specifically detects *L. monocytogenes* genomic cluster IIB strains, wherein said isolated nucleic acid molecule comprises a sequence that is at least 90% identical to (a) SEQ ID NO:1 or the complement thereof; (b) nucleotides 374–2017 of SEQ ID NO:1 or the complement thereof; (c) nucleotides 2031–2975 of SEQ ID NO:1 or the complement thereof, or (d) a fragment of SEQ ID NO:1 that is 50 to 3060 nucleotides in length or the complement.

2. The isolated nucleic acid molecule of claim 1, wherein said isolated nucleic acid molecule comprises a sequence that is at least 90% identical to (a) SEQ ID NO:1, or the complement thereof, (b) nucleotides 374–2017 of SEQ ID NO:1 or the complement thereof, or (c) nucleotides 2031–2975 of SEQ ID NO:1 or the complement thereof.

3. The isolated nucleic acid molecule of claim 1, wherein said isolated nucleic acid molecule comprises the sequence of SEQ ID NO:1 or the complement thereof.

4. The isolated nucleic acid molecule of claim 1, wherein said isolated nucleic acid molecule comprises the sequence of SEQ ID NO:1.

5. The isolated nucleic acid molecule of claim 1, further comprising a vector.

6. The isolated nucleic acid of claim 5, wherein said sequence is operably linked to control sequences recognized by a host cell transformed with the vector.

7. A host cell comprising the isolated nucleic acid molecule of claim 6.

8. The host cell of claim 7, wherein said cell is a CHO cell, an *E. coli* or a yeast cell.

9. An isolated nucleic acid molecule that comprising DNA that hybridizes under stringent conditions to (a) SEQ ID NO:1 or the complement thereof; or (b) a fragment of SEQ ID NO:1 that is 50 to 3060 nucleotides in length of the complement thereof.

10. The isolated nucleic acid molecule of claim 9, wherein said isolated nucleic acid molecule specifically detects *L. monocytogenes* serotype 4b.

11. An isolated nucleic acid molecule that specifically detects *L. monocytogenes* genomic cluster IIB strains, wherein said isolated nucleic acid molecule comprises a sequence that (a) encodes the amino acid sequence encoded by nucleotides 374 to 2017 of SEQ ID NO:1, or (b) is the complement of said sequence that encodes the amino acid sequence encoded by nucleotides 374 to 2017 of SEQ ID NO:1.

12. An isolated nucleic acid molecule comprising a sequence that (a) encodes the amino acid sequence encoded by nucleotides 2031 to 2975 of SEQ ID NO:1, or (b) is the complement of said sequence that encodes the amino acid sequence encoded by nucleotides 2031 to 2975 of SEQ ID NO:1.

* * * * *

SEQUENCE LISTING

<160> NUMBER OF SEQ ID NOS: 7

<210> SEQ ID NO 1
<211> LENGTH: 3060
<212> TYPE: DNA
<213> ORGANISM: Bacterial

<400> SEQUENCE: 1

```
caaagagtga tttatctggc aggcaaaacg ttgtctaact agtaaattta aagcgagtcc      60
ttatcttttt caagtaaggg ctcgctttaa atttcaattg cgctagcatc ttttttttgc     120
tatattaaag gatagtaacg tctcatatag ggagtggaga aaaagagtgt taaataaaaa     180
aagagttata gttggggttt tgctactatt actaagttta atttctatta gctattattc     240 agaaacctttt aaactaactt taagctggtt gttatttgca gtagttttaa cggttcttta    300
```

-continued

| | |
|---|---|
| ttttagacaa gagaaaaact ttcaatttca atggtcaaca ttgataacct cactaataat | 360 |
| tagtttattt tggatggctt catcattcaa tggtggacca tatggcggga attttgtttt | 420 |
| taatagtatt attttagcag gaacttttct tgtaatcact atctttgttt tacttttatt | 480 |
| acttgaaatg cgaacggaat ataaagcaag accgaatcgc aaagtaaaat ggccattttt | 540 |
| cgcactattt acgagtattc cattcgtggt ctggatgatt tcatttctag cctattatcc | 600 |
| agcaaaaatg acatttgact cctattacca atggggaatg gctcacggta ttcgccaata | 660 |
| tagtcagtgg catccgcttt tacacacttt gtggatagaa acaacaagtg cgatttacga | 720 |
| ctcaccttcg agttacattt tttctcaaat aattgttgtt tcattaatcg ttggctttgc | 780 |
| tatttatact cttgtaaaaa tgggcgcgca tatttggatt ggtgtttgta tttcaatcgg | 840 |
| ctatgccatt taccctgcag caatgtttta ttctgcaaca gcatggaaag attttccatt | 900 |
| tgcagccttt atattacttt tcaccgtttt aattttaaaa atagtacaat ctaatggaat | 960 |
| gtggctgaaa aattggtggc acctatcgc ttttgtttta gtagcttttg tttgtataaa | 1020 |
| tttacgaaac aatggaatga tgattatcat cgtatcgctt ctgtgcttgc ttattttcat | 1080 |
| gaaaaacttt cgtcttatta ttaccggtat tcttgttgga accttgggac tgaattttt | 1140 |
| atttggtctg gttatgacaa acgggcttaa tgcgcaacct aatccattaa accaagcgct | 1200 |
| agcaattcct tcccaacaaa ttggggctac ttttacaat gatggaaact ttactcctga | 1260 |
| attaaaagag tatttcactt ccatattacc tgaagaaat tggaaaaaag attacaaccc | 1320 |
| ttatactgta gacccaatta agcatgatac caaatacaat tcatccgtca ttgaagatga | 1380 |
| ttttggacta tacattaaaa attggttcaa actcttaacg gctaatttcg gtacttatgt | 1440 |
| aggggcttat ttagatcaaa cagcagtcat ttggcaattc tattctccag aaaattataa | 1500 |
| agtattcttt gatacttcag cgaatattca agatacaaga tatgatgtga gagcattcgc | 1560 |
| caaattcttc ccagaaggtt tatcggaaga agagattaat aaattaggat atgaagtcta | 1620 |
| tcaaaatgaa tacaaaaatg caactggaaa agatgctgtt agctacaatg agtataagag | 1680 |
| acggattgat gactctacta atccccttat ttcaatatct aaagctccaa gtctgaagaa | 1740 |
| aataacagat agcatttatg caaaaacaac aaatgagtgg caaaattatt tattaaaagg | 1800 |
| agccattcca ttagtattgc tcataatagc aattgctgcc gtctgcctcc aacgtcctaa | 1860 |
| aaagaaactt cttatttttg cacctgtagt aatggcactt attactatag caatcgcaat | 1920 |
| gccagcaaca gactttagat attcttatag ttttatttc accgtgccta ttgtctttt | 1980 |
| tgcaactaaa ttaaaaaatt acaagaaaa tcaattttaa ggagagaata tgggaattc | 2040 |
| taaatgagaa agtagctgta ctcttgcctt gttataacga ggagcttaca attggtaagg | 2100 |
| taattgatga ttttaagaaa gaattaccaa atgcggatat ttatgtgtac gacaataatt | 2160 |
| ctaaagataa aacctttgaa atagcgaaag atcatggtgc tatcgttcga aaagaaatgc | 2220 |
| gccaaggtaa aggtaatgta gtacgttcta tgttcgcgga tatagatgct gattactatt | 2280 |
| taatggtcga tggtgacgat acctatccag cagaatactg ccatgaaata ttagaggtgc | 2340 |
| ttcgcaataa ggaagctaat atggttattg gtgatcgtct gagtaatggt acctacactg | 2400 |
| aagaaaataa aagaaatttt catgactttg gtaactcact agtacgtaat acaattaatc | 2460 |
| gtatcttcaa aagtaatttg agagatatca tgacaggcta ccgtggcttt gatcgttatt | 2520 |
| ttgttaagac tatgccagtt ttaagccctg gttttgagat tgaaactgag atgagcattc | 2580 |
| acgcattgga aaatcgcttt ttagtgaaag aaattgaaat tgattaccgt gatcgtccag | 2640 |
| aaggtagtga atcaaaacta aacactttt ctgatggttt caagtaatt atgacgattg | 2700 |

-continued

```
taagattatt taaaaatagt cgtccgtttt tatttttcaa tttattagcc tctttgtttg    2760
tgcttgtagg agttctagtt ggtttgccag tcataattca gtttgctcaa attggcttgg    2820
tactaaaatt tccgagtgca ttacttgcaa ctggtttaat cataatgggt atgctgttct    2880
tcatttgtgg attaatcctt gatacgatag ctcatagaag cagacaaagc tacttcttag    2940
aacttgttaa ataccgcgaa agaaatccat tgaactaaag ttagccaata aaagagtcga    3000
tttcctaatt caggaaatcg actcttttat ttatatcggt actacaattg ttctactgtt    3060
```

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic

<400> SEQUENCE: 2
tcatcgtatc gcttctgtg                                                   19

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 3
gtgccattac tacaggtgca                                                  20

<210> SEQ ID NO 4
<211> LENGTH: 549
<212> TYPE: PRT
<213> ORGANISM: Bacterial

<400> SEQUENCE: 4

Met Ala Ser Ser Phe Asn Gly Gly Pro Tyr Gly Gly Asn Phe Val Phe
 1               5                  10                  15

Asn Ser Ile Ile Leu Ala Gly Thr Phe Leu Val Ile Thr Ile Phe Val
                20                  25                  30

Leu Leu Leu Leu Leu Glu Met Arg Thr Glu Tyr Lys Ala Arg Pro Asn
            35                  40                  45

Arg Lys Val Lys Trp Pro Phe Phe Ala Leu Phe Thr Ser Ile Pro Phe
        50                  55                  60

Val Val Trp Met Ile Ser Phe Leu Ala Tyr Tyr Pro Ala Lys Met Thr
    65                  70                  75                  80

Phe Asp Ser Tyr Tyr Gln Trp Gly Met Ala His Gly Ile Arg Gln Tyr
                85                  90                  95

Ser Gln Trp His Pro Leu Leu His Thr Leu Trp Ile Glu Thr Thr Ser
            100                 105                 110

Ala Ile Tyr Asp Ser Pro Ser Ser Tyr Ile Phe Ser Gln Ile Ile Val
        115                 120                 125

Val Ser Leu Ile Val Gly Phe Ala Ile Tyr Thr Leu Val Lys Met Gly
    130                 135                 140

Ala His Ile Trp Ile Gly Val Cys Ile Ser Ile Gly Tyr Ala Ile Tyr
145                 150                 155                 160

Pro Ala Ala Met Phe Tyr Ser Ala Thr Ala Trp Lys Asp Phe Pro Phe
                165                 170                 175

Ala Ala Phe Ile Leu Leu Phe Thr Val Leu Ile Leu Lys Ile Val Gln

```
              180                 185                 190
Ser Asn Gly Met Trp Leu Lys Asn Trp Trp His Leu Ile Ala Phe Val
        195                 200                 205

Leu Val Ala Phe Val Cys Ile Asn Leu Arg Asn Asn Gly Met Met Ile
210                 215                 220

Ile Ile Val Ser Leu Leu Cys Leu Leu Ile Phe Met Lys Asn Phe Arg
225                 230                 235                 240

Leu Ile Ile Thr Gly Ile Leu Val Gly Thr Leu Gly Leu Asn Phe Leu
                245                 250                 255

Phe Gly Leu Val Met Thr Asn Gly Leu Asn Ala Gln Pro Asn Pro Leu
                260                 265                 270

Asn Gln Ala Leu Ala Ile Pro Ser Gln Gln Ile Gly Ala Thr Phe Tyr
                275                 280                 285

Asn Asp Gly Asn Phe Thr Pro Glu Leu Lys Glu Tyr Gly Thr Ser Ile
                290                 295                 300

Leu Pro Glu Glu Asn Trp Lys Lys Asp Tyr Asn Pro Tyr Thr Val Asp
305                 310                 315                 320

Pro Ile Lys His Asp Thr Lys Tyr Asn Ser Ser Val Ile Glu Asp Asp
                325                 330                 335

Phe Gly Leu Tyr Ile Lys Asn Trp Phe Lys Leu Leu Thr Ala Asn Phe
                340                 345                 350

Gly Thr Tyr Val Gly Ala Tyr Leu Asp Gln Thr Ala Val Ile Trp Gln
                355                 360                 365

Phe Tyr Ser Pro Glu Asn Tyr Lys Val Phe Phe Asp Thr Ser Ala Asn
                370                 375                 380

Ile Gln Asp Thr Arg Tyr Asp Val Arg Ala Phe Ala Lys Phe Phe Pro
385                 390                 395                 400

Glu Gly Leu Ser Glu Glu Ile Asn Lys Leu Gly Tyr Glu Val Tyr
                405                 410                 415

Gln Asn Glu Tyr Lys Asn Ala Thr Gly Lys Asp Ala Val Ser Tyr Asn
                420                 425                 430

Glu Tyr Lys Arg Arg Ile Asp Asp Ser Thr Asn Pro Leu Ile Ser Ile
                435                 440                 445

Ser Lys Ala Pro Ser Leu Lys Lys Ile Thr Asp Ser Ile Tyr Ala Lys
450                 455                 460

Thr Thr Asn Glu Trp Gln Asn Tyr Leu Leu Lys Gly Ala Ile Pro Leu
465                 470                 475                 480

Val Leu Leu Ile Ile Ala Ile Ala Ala Val Cys Leu Gln Arg Pro Lys
                485                 490                 495

Lys Lys Leu Leu Ile Phe Ala Pro Val Val Met Ala Leu Ile Thr Ile
                500                 505                 510

Ala Ile Ala Met Pro Ala Thr Asp Phe Arg Tyr Ser Tyr Ser Phe Ile
                515                 520                 525

Phe Thr Val Pro Ile Val Phe Phe Ala Thr Lys Leu Lys Asn Tyr Lys
                530                 535                 540

Glu Asn Gln Phe Glx
545

<210> SEQ ID NO 5
<211> LENGTH: 316
<212> TYPE: PRT
<213> ORGANISM: Bacterial

<400> SEQUENCE: 5
```

```
Met Gly Ile Leu Asn Glu Lys Val Ala Val Leu Leu Pro Cys Tyr Asn
  1               5                  10                  15

Glu Glu Leu Thr Ile Gly Lys Val Ile Asp Asp Phe Lys Lys Glu Leu
             20                  25                  30

Pro Asn Ala Asp Ile Tyr Val Tyr Asp Asn Ser Lys Asp Lys Thr
             35                  40                  45

Phe Glu Ile Ala Lys Asp His Gly Ala Ile Val Arg Lys Glu Met Arg
         50                  55                  60

Gln Gly Lys Gly Asn Val Val Arg Ser Met Phe Ala Asp Ile Asp Ala
 65              70                  75                  80

Asp Tyr Tyr Leu Met Val Asp Gly Asp Thr Tyr Pro Ala Glu Tyr
             85                  90                  95

Cys His Glu Ile Leu Glu Val Leu Arg Asn Lys Glu Ala Asn Met Val
            100                 105                 110

Ile Gly Asp Arg Leu Ser Asn Gly Thr Tyr Thr Glu Glu Asn Lys Arg
            115                 120                 125

Asn Phe His Asp Phe Gly Asn Ser Leu Val Arg Asn Thr Ile Asn Arg
130             135                 140

Ile Phe Lys Ser Asn Leu Arg Asp Ile Met Thr Gly Tyr Arg Gly Phe
145             150                 155                 160

Asp Arg Tyr Phe Val Lys Thr Met Pro Val Leu Ser Pro Gly Phe Glu
                165                 170                 175

Ile Glu Thr Glu Met Ser Ile His Ala Leu Glu Asn Arg Phe Leu Val
            180                 185                 190

Lys Glu Ile Glu Ile Asp Tyr Arg Asp Arg Pro Glu Gly Ser Glu Ser
            195                 200                 205

Lys Leu Asn Thr Phe Ser Asp Gly Phe Lys Val Ile Met Thr Ile Val
        210                 215                 220

Arg Leu Phe Lys Asn Ser Arg Pro Phe Leu Phe Asn Leu Leu Ala
225             230                 235                 240

Ser Leu Phe Val Leu Val Gly Val Leu Val Gly Leu Pro Val Ile Ile
                245                 250                 255

Gln Phe Ala Gln Ile Gly Leu Val Leu Lys Phe Pro Ser Ala Leu Leu
            260                 265                 270

Ala Thr Gly Leu Ile Ile Met Gly Met Leu Phe Ile Cys Gly Leu
            275                 280                 285

Ile Leu Asp Thr Ile Ala His Arg Ser Arg Gln Ser Tyr Phe Leu Glu
        290                 295                 300

Leu Val Lys Tyr Arg Glu Arg Asn Pro Leu Asn Glx
305             310                 315
```

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic

<400> SEQUENCE: 6
cggaattccg tgaagtatct tcctacag                                    28

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic

```
<400> SEQUENCE: 7
caggaaacag ctatgaccat gatt                                              24
```